(12) United States Patent
Roberts et al.

(10) Patent No.: US 7,263,156 B2
(45) Date of Patent: Aug. 28, 2007

(54) METHOD AND APPARATUS TO FACILITATE COMPUTERIZED TOMOGRAPHY OF RELATIVELY LARGE OBJECTS

(75) Inventors: Barry R. Roberts, Gurnee, IL (US); Charles Smith, Libertyville, IL (US); James M. McNally, Grayslake, IL (US)

(73) Assignee: Varian Medical Systems Technologies, Inc., Palo Alto, CA (US)

( * ) Notice: Subject to any disclaimer, the term of this patent is extended or adjusted under 35 U.S.C. 154(b) by 169 days.

(21) Appl. No.: 11/127,431

(22) Filed: May 12, 2005

(65) Prior Publication Data

US 2006/0256913 A1 Nov. 16, 2006

(51) Int. Cl.
*G01N 23/083* (2006.01)

(52) U.S. Cl. .......................... 378/14; 378/15
(58) Field of Classification Search .................. 378/14, 378/15
See application file for complete search history.

(56) References Cited

U.S. PATENT DOCUMENTS

| | | | |
|---|---|---|---|
| 4,422,177 A * | 12/1983 | Mastronardi et al. ......... | 378/17 |
| 4,637,040 A | 1/1987 | Sohval et al. | |
| 5,032,990 A | 7/1991 | Eberhard et al. | |
| 5,319,693 A * | 6/1994 | Eberhard et al. ............. | 378/19 |
| 5,917,876 A * | 6/1999 | Fujii et al. ..................... | 378/4 |
| 6,430,253 B1 * | 8/2002 | Oikawa ....................... | 378/15 |
| 6,618,467 B1 * | 9/2003 | Ruchala et al. ............... | 378/65 |
| 7,046,757 B1 * | 5/2006 | Bani-Hashemi et al. ....... | 378/7 |
| 2002/0109532 A1 | 8/2002 | Nakada | |

* cited by examiner

*Primary Examiner*—Edward J. Glick
*Assistant Examiner*—Thomas R. Artman
(74) *Attorney, Agent, or Firm*—Fitch, Even, Tabin & Flannery

(57) ABSTRACT

A computerized tomography process (100) that provides, optionally, for preliminary scans (101), helically-oriented full scans (102), and/or improved resolution scans (103). In some instances, partial cross-sectional views are captured which views are then later joined to yield a complete view. In some instances a helical image-capture path is used. In yet other instances small lateral shifts to the position of the X-ray source are used to provide higher resolution views of the object being scanned.

14 Claims, 6 Drawing Sheets

METHOD AND APPARATUS TO FACILITATE COMPUTERIZED TOMOGRAPHY OF RELATIVELY LARGE OBJECTS

TECHNICAL FIELD

This invention relates generally to computerized tomography and more particularly to computerized tomography of relatively large-sized objects.

BACKGROUND

It is known to use X-ray sources to obtain computerized tomography images. In many prior art applications (and particularly in the field of medical applications) the object being scanned lies fully within the X-ray source fan angle. There are situations, however, when computerized tomography images for relatively larger objects are desired (for objects such as, but not limited to, automobiles and/or larger automobile components, rocket motors, cargo containers, and so forth); i.e., objects that are larger than the available X-ray source fan angle. Also in many prior art applications, the object (such as a human body) comprises a relatively soft or less opaque object, thus requiring smaller amounts of X-ray energy to obtain useful images. There are again situations, however, when computerized tomography images for relatively larger, harder, more opaque objects are desired (again for objects such as, but not limited to, automobiles and their components, rocket motors, cargo containers, and so forth). Considerably higher amounts of X-ray energy are typically required to obtain useful images with such objects.

The challenges become particularly acute when these two problems coincide; that is, when a relatively large object also comprises a relatively opaque object. It becomes quickly impractical (economically and/or physically) to provide a large enough X-ray source to provide both sufficient power and a sufficiently large X-ray source fan angle to accommodate such objects. By one prior art approach, larger objects are scanned using translate/rotate geometries in conjunction with high energy X-ray sources. Such systems often employ detector designs having relatively small apertures as compared to their corresponding detector pitch (often known as small aperture/large pitch detectors) in order to attempt to provide high spatial resolution and good image quality. Unfortunately, such an approach occasions numerous problems including, but not limited to, large and complex mechanical configurations, alignment and accuracy challenges, relatively slow scanning speed, difficulty with or an inability to scan an object in an optimum position for that object, and non-flow through system operation to name a few.

Rotate only geometries have also been proposed (particularly for tangential scanning modes when scanning rocket motors). This approach fails to provide accurate whole object images and typically only accommodates circularly symmetrical objects. Also, this approach only provides accurate images of circumferential details in the outer annulus of the object; radial details and inner ring details are incorrectly imaged.

BRIEF DESCRIPTION OF THE DRAWINGS

The above needs are at least partially met through provision of the method and apparatus to facilitate computerized tomography of relatively large objects described in the following detailed description, particularly when studied in conjunction with the drawings, wherein.

Figure 1:
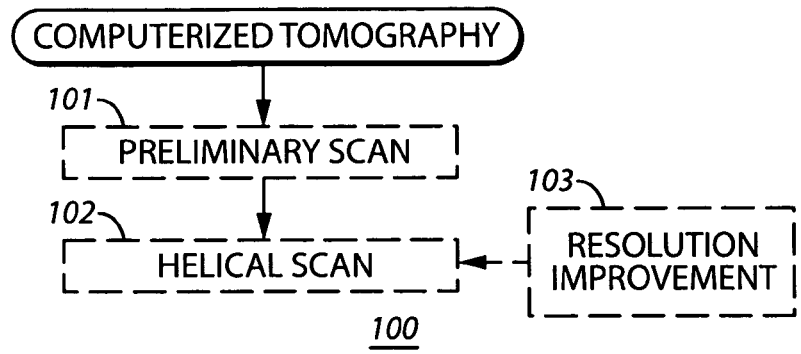
FIG. 1 comprises a flow diagram as configured in accordance with various embodiments of the invention.

Skilled artisans will appreciate that elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments of the present invention. It will further be appreciated that certain actions and/or steps may be described or depicted in a particular order of occurrence while those skilled in the arts will understand that such specificity with respect to sequence is not actually required. It will also be understood that the terms and expressions used herein have the ordinary meaning as is accorded to such terms and expressions with respect to their corresponding respective areas of inquiry and study except where specific meanings have otherwise been set forth herein.

DETAILED DESCRIPTION

Generally speaking, pursuant to these various embodiments, various aspects of computerized tomography are supported to facilitate corresponding X-ray images of relatively larger objects. In a preferred approach, an object to be scanned is substantially continuously moved (preferably along an axis thereof). During this movement, an X-ray source of radiation and at least one corresponding radiation detector are moved about the object's axis in a substantially continuous and concentric fashion. So configured, the X-ray source of radiation essentially moves in a helical manner about and with respect to the object. Although any given captured image will not provide a complete view of the object's full cross-section (presuming that the object comprises a relatively large object), such images will well support the use of interpolation techniques and will typically yield an acceptable study of the object.

Also pursuant to a preferred approach, and again, while substantially continuously causing movement of the object, a determination can be made regarding whether to adjust a relative lateral position of the X-ray beam (via, for example, steering of the X-ray beam on, for example, a sample-by-sample basis) with respect to the above-mentioned detector to thereby improve resolution of a corresponding computerized tomography image. This approach, when practiced, can aid in at least ameliorating the Nyquist sampling failures and corresponding aliasing artifacts that are otherwise often associated with the use of small aperture/large pitch detectors that are otherwise usefully employed to obtain good scatter rejection.

Pursuant to yet another aspect of a preferred approach, a preliminary scan is accommodated. In particular, and particularly when employed with objects having a cross-sectional girth that exceeds the illumination pattern of the X-ray beam, a plurality of line scan images of a first portion (such as an upper half) of the object are obtained while moving the object and maintaining the source/detector relatively stationary. The source/detector are then moved to a new position (one that is preferably 180 degrees opposite to the first position) and a new plurality of line scan images are obtained for a second portion of the object (such as a lower half of the object) while again moving the object. In a preferred approach, the first set of line scan images are matched with their corresponding images of the second set of line scan images to yield a set of complete-object line scan images.

So configured, large objects of various shapes and sizes are readily accommodated. These teachings are also readily deployed with relatively large X-ray sources (including linear accelerators providing 1 million volts or more of output X-ray radiation) thereby assuring that even large, relatively opaque objects can be successfully scanned. Those skilled in the art will appreciate that these teachings offer smaller, less complex mechanical configurations than many prior art offerings while assuring equal or better alignment and accuracy. Increased scanning speeds are also attainable. Also, these teachings are relatively neutral with respect to object orientation. This permits many objects to be scanned while in an optimum position for the object rather than requiring the object to be oddly or inappropriately positioned in order to accommodate the scanning equipment.

These and other benefits may become clearer upon making a thorough review and study of the following detailed description. Referring now to the drawings, and in particular to FIG. 1, these teachings make provision for a process 100 that supports an optional preliminary scan 101. Such preliminary scans, usually a plurality of line scan images, typically comprise a two dimensional radiographic view of a given object rather than the three dimensional view from a full computerized tomography scan. Preliminary scans can serve, for example, to identify one or more locations of an object that warrant more complete computerized tomography. When conducting a more complete scan, these teachings also support the optional use of a helical scan 102. Also, when desired and/or otherwise appropriate, this process 100 can optionally support resolution improvement 103. Each of these processes is described in more detail below.

Figure 2:
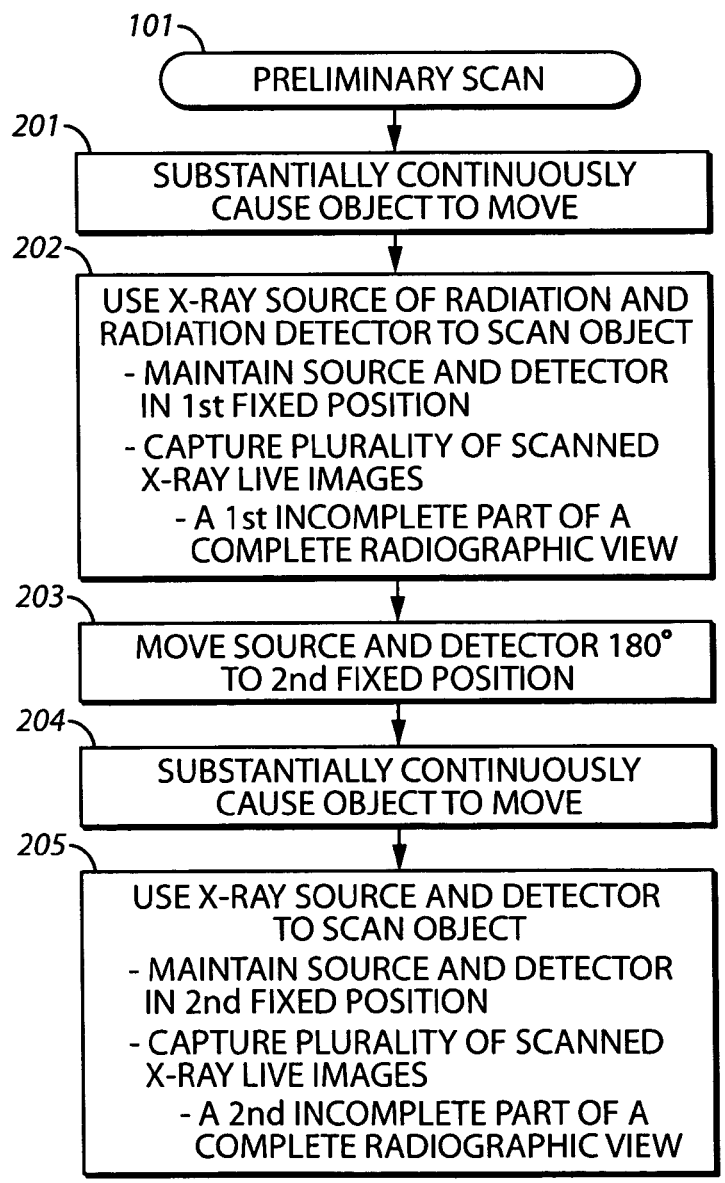
FIG. 2 comprises a flow diagram as configured in accordance with various embodiments of the invention.

Referring now to FIG. 2, the preliminary scan 101 can comprise a preliminary scan as is taught by the prior art when the object to be scanned has a cross-sectional girth that is well accommodated by the illumination pattern of the X-ray beam being used. When the object has a cross-sectional girth that is larger than the available X-ray beam illumination pattern, however, this preliminary scan 101 can comprise causing 201 substantially continuous movement of the object in a first direction. In a preferred approach, the object has an axis of interest (such as a longitudinal axis) and the described movement is in the direction of that axis of interest. Other directionality, however, may be employed to suit the needs and/or requirements of a given setting.

Figure 3:
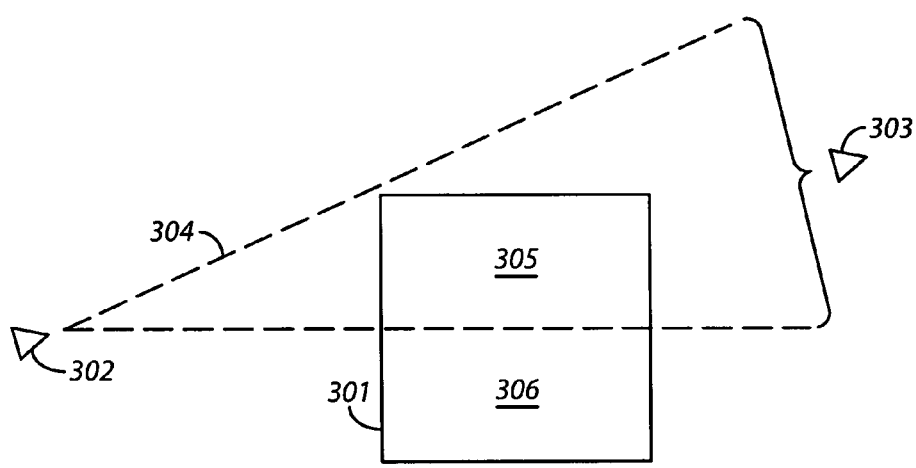
FIG. 3 comprises a side elevational schematic depiction as configured in accordance with various embodiments of the invention.

While the object so moves, this process then provides for using 202 an X-ray source of radiation and at least one radiation detector to conduct the preliminary scan of the object. More particularly, and pursuant to a preferred approach, the X-ray source of radiation and the radiation detector are maintained in a substantially fixed first position while the radiation detector captures a plurality of scanned X-ray line images (it would also be possible, if desired, to have the source and detector also translate with respect to the axis of interest; such translation can occur, for example, in an opposite direction to the object translation to thereby reduce the absolute speed of the object). Since the object has a cross-sectional girth that is larger than the available X-ray source fan angle, these line images comprise only an incomplete radiographic view of the object. To illustrate, and referring momentarily to FIG. 3, when the object 301 is larger than the X-ray beam's illumination pattern 304, the X-ray source 302 and detector 303 are positioned to capture radiographic line images of a first portion 305 of the object 301 while missing a remaining portion 306 of the object 301.

In a preferred approach, a number of such line images are captured as the object moves, thereby providing a number of corresponding partial-object X-ray line images. The distance between such images can be varied with the needs and/or desires of the operator.

Upon concluding this first round of image capture activity, and referring again to FIG. 2, this process then provides for moving 203 the X-ray source of radiation and preferably the radiation detector to a substantially dissimilar second position. (It would be possible to provide multiple detectors to thereby avoid significant movement of this component, but in general such an approach may contribute unduly to the overall mechanical and operational complexity of the resultant apparatus. Note also that multiple detectors in the lateral direction generate line images at different angles and thus make it difficult to select the area of interest for further computerized tomography analysis). In a preferred approach, these components are moved to a second position that is offset from the first position by 180 degrees. To illustrate, and referring momentarily to FIG. 3, the X-ray source 302 can be moved to a position that is substantially 180 degrees opposite to the initial position.

Figure 4:
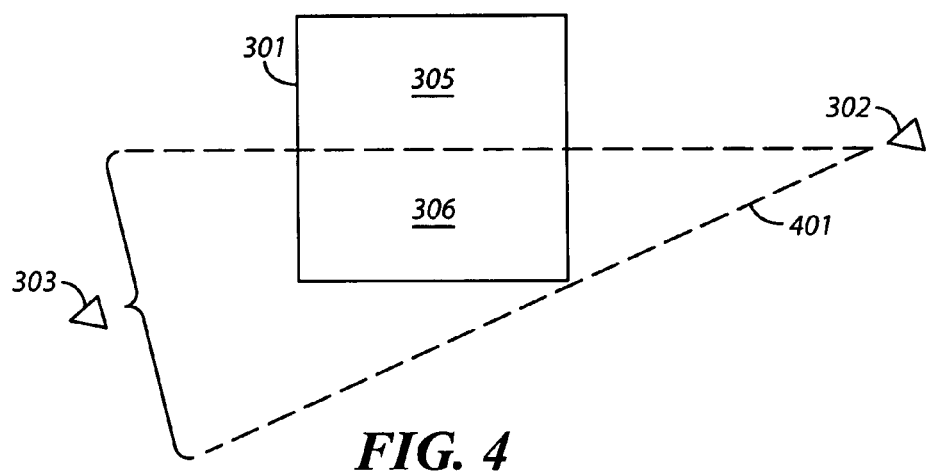
FIG. 4 comprises a side elevational schematic depiction as configured in accordance with various embodiments of the invention.

Referring again to FIG. 2, and again while causing 204 the object to substantially continuously move, the X-ray source and detector are then again used 205 to continue the preliminary scan of the object. In particular, and while maintaining the X-ray source of radiation and the detector in the described second position, these elements are used to capture a second plurality of scanned X-ray line images. Again, since the object has a cross-section girth that is wider than the available X-ray beam, the resultant line images will each only comprise an incomplete cross-sectional view of the object. By appropriate positioning of the source/detector as described, however, those skilled in the art will appreciate that the line images as comprise the first plurality of images can be readily joined to the corresponding line images as comprise the second plurality of images. So joined, each pair of juxtaposed line images will comprise a complete radiographic view of the object. To illustrate, and referring again to FIG. 4, the second set of images will capture a portion 306 of the object 301 that was previously missed. Accordingly, images of the upper portion 305 of the object 301 are joined to corresponding images of the lower portion 306 of the object 301 to yield a resultant complete cross-sectional view of the object 301.

In general, it is preferred that each image pair to be joined share a common axial view of the object. It would be possible, of course, to permit some degree of overlap as between the two images and then arrange for appropriate cropping during an image joiner process. It would also be possible to provide a gap between the two images to accommodate some special need or circumstance.

Those skilled in the art will appreciate that such a preliminary scan can be effected in a relatively brief period of time. Additional time savings are possible when the second series of images are captured during movement of the object back to its original position (thereby avoiding the time required to return the object to its original starting point before initiating the second series of scans). It will also be understood that these teachings are readily applied to objects having a wide variety of form factors.

Figure 5:
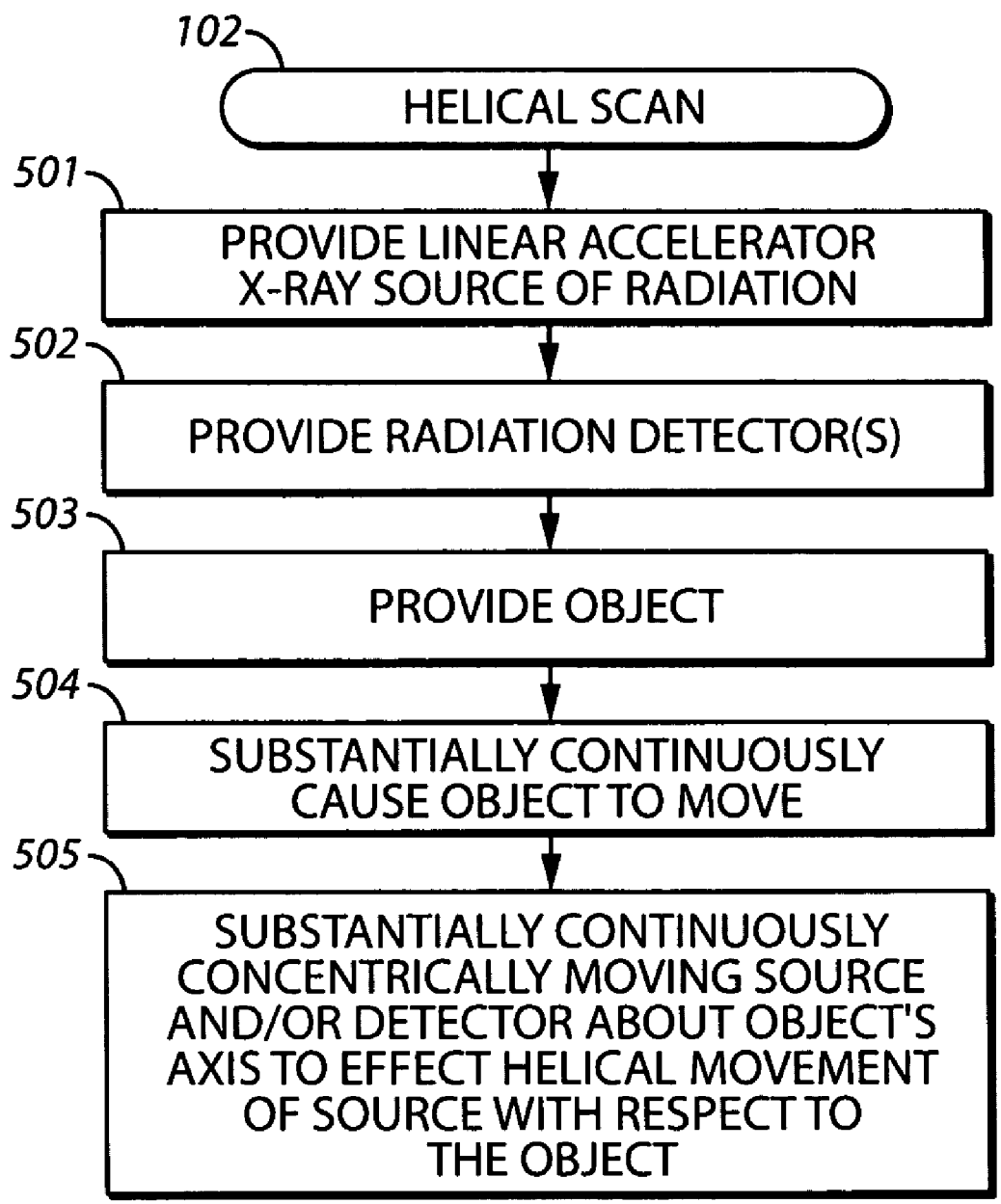
FIG. 5 comprises a flow diagram as configured in accordance with various embodiments of the invention.

Referring now to FIG. 5, the helical scan process 102 will be described. Again presuming the provision of an X-ray source of radiation 501 and at least one radiation detector 502, and the provision 503 of an object to be scanned, the object is again substantially continuously caused to move. And again, in a preferred approach, the object is caused to move along a given axis thereof. During this movement of the object, the X-ray source of radiation and the radiation detector are used 505 to acquire a plurality of computerized tomography images of the object by substantially continuously concentrically moving at least the X-ray source of radiation about an axis of the object to effect helical movement of the X-ray source of radiation with respect to the object.

Figure 6:
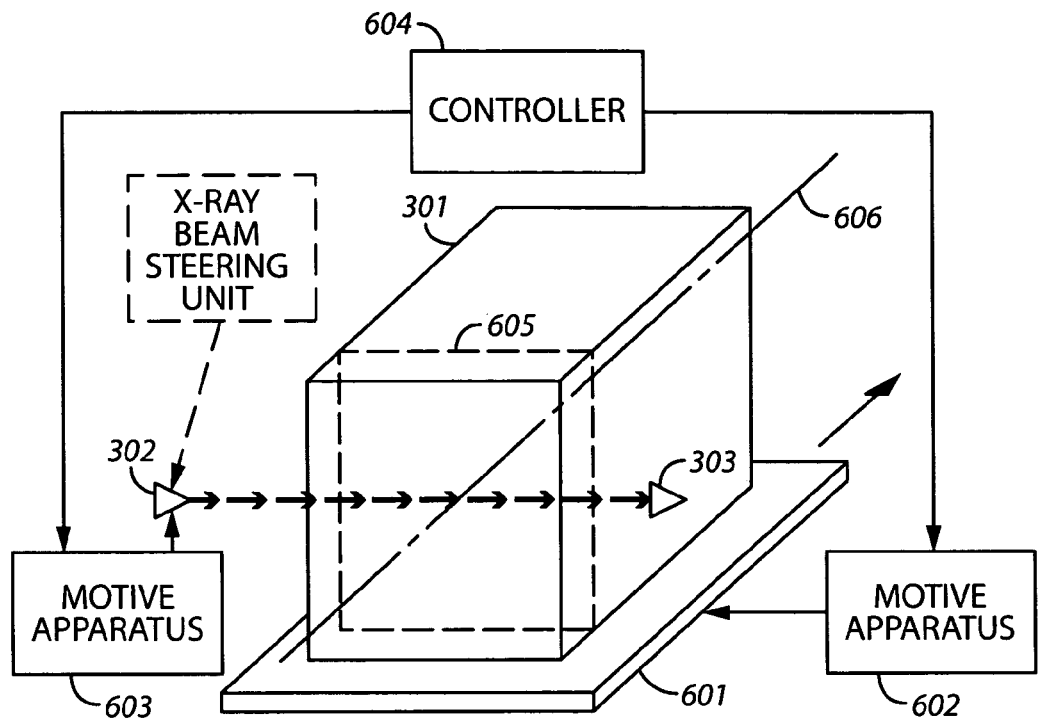
FIG. 6 comprises a perspective schematic depiction as configured in accordance with various embodiments of the invention.
Figure 7:
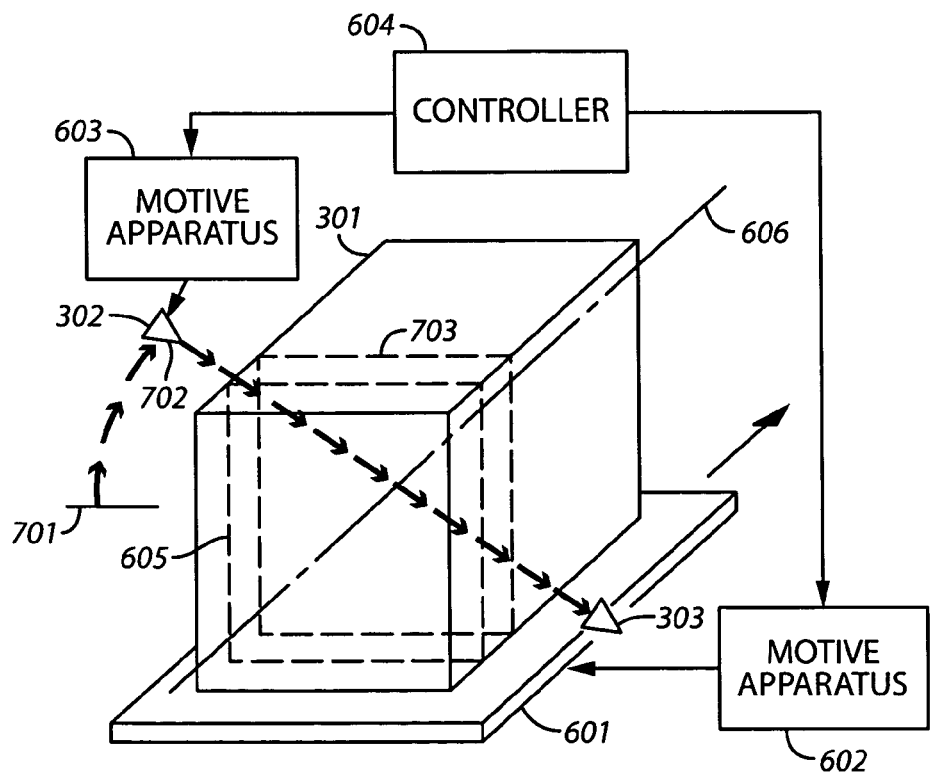
FIG. 7 comprises a perspective schematic depiction as configured in accordance with various embodiments of the invention.

These concepts are perhaps better illustrated in FIGS. 6 and 7. In FIG. 6, an object 301 is disposed atop an object receiver 601 such as a movable pallet. A motive apparatus 602 (such as one or more motors, gears, clutch assemblies, or the like as are well understood in the art) operably couples to the object receiver 601 to facilitate selective movement of the object receiver 601, and hence the object 301. Another motive apparatus 603 operably couples to the X-ray source of radiation 302 to permit selective movement of the X-ray source of radiation 302 about the object 301. In a preferred approach this movement comprises radial movement about an axis 606 of the object 301. Also in a preferred embodiment, the second motive apparatus 603 also operably couples to the radiation detector(s) 303 such that the radiation detector 303 and the X-ray source of radiation 302 move in tandem with one another.

So configured, the source/detector can move in a circle about the object 301 while the object 301 moves axially with respect to the source/detector. (It would also be possible, if desired, to have the source and detector also translate with respect to the axis of interest; such translation can occur, for example, in an opposite direction to the object translation to thereby reduce the absolute speed of the object.) In a preferred approach, a controller 604 operably couples to the motive apparatus 602 and 603 and serves to control the respective movement of the object receiver 601 and the X-ray source 302 and detector 303. Those skilled in the art will appreciate that this controller 604 can comprise a single platform or can be distributed over a plurality of enabling platforms. Those skilled in the art will further understand that such a controller 604 can comprise a dedicated and fixed purpose platform or can be partially or wholly programmable with respect to its functionality and purpose.

As illustrated in FIG. 6, the object 301 and source/detector 302/303 have a first respective position with respect to one another. A first computerized tomographic image taken at this point will yield an image that corresponds to a first cross-sectional portion 605 of the object 301. Of course, when the cross-sectional girth of the object 301 exceeds the X-ray source fan angle, the resultant image will not comprise a complete view of that cross section.

Figure 8:
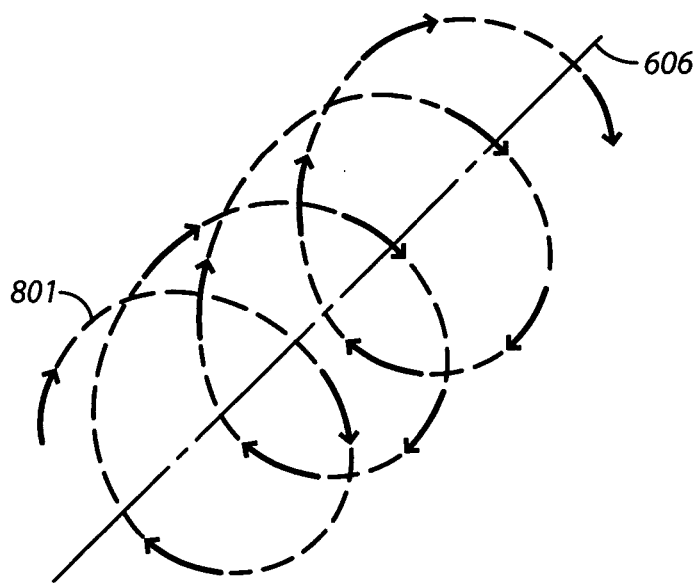
FIG. 8 comprises a perspective schematic depiction as configured in accordance with various embodiments of the invention.

Pursuant to a preferred approach, and referring now to FIG. 7, upon moving the object 301 to a new position (using the object receiver 601) and the X-ray source 302 and detector 303 to a new position 702, a second cross-sectional image corresponding to a second cross section 703 of the object 301 is captured. In this embodiment, the angular displacement between the second position 702 of the X-ray source 302 and the starting position 701 is considerably less than the 180 degree displacement used during the above-described preliminary scan. The particular angular displacement selected for use in a given setting will vary with the needs and requirements of that setting in addition to accounting for any relevant system limitations as may be present. In a preferred approach, one might select from between one and pi times the number of detector samples to cover the object for the number of angular samples. In general, the larger the number of angular samples the better the resolution toward the object's edge. This process can continue until the object 301 has been fully scanned. With reference to FIG. 8, it can be seen that the effective path 801 of the source/detector with respect to the axis 606 of movement of the object itself comprises a helical path. Note that modified helical paths like the so-called saddle trajectory can also be used. A saddle scan comprises a helical trajectory that is performed in both of two directions, where the forward and reverse directions of the helix do not coincide thus improving lateral resolution and image quality.

The amount of movement permitted the object between scans can impact image quality when working with large objects as each image will necessarily constitute an incomplete cross-sectional view. In such a case, however, an interpolation process can be employed to provide any missing data so long as the effective helical pitch is not too great.

Figure 9:
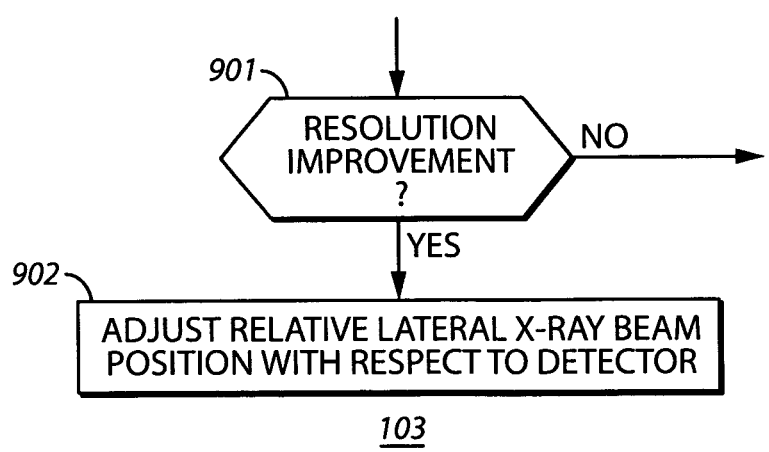
FIG. 9 comprises a flow diagram as configured in accordance with various embodiments of the invention.

FIG. 6 also depicts an optional X-ray beam steering unit 607. This X-ray beam steering unit 607 can serve to adjust a relative lateral position of the X-ray beam with respect to the detector 303 to thereby improve resolution of a corresponding computerized tomography image. This unit 607 can serve, for example, to facilitate the resolution improvement capability 103 mentioned earlier. With reference to FIG. 9, this process can comprise, for example, a determination 901 regarding whether to adjust a relative lateral position of the X-ray beam with respect to at least one detector to thereby improve resolution of at least one computerized tomography image. This determination can be based, for example, upon identifying when an operator has selected this mode of operation. If desired, this capability can also be optionally triggered by some detected or calculated event or condition of choice.

Upon determining to effect such resolution improvement, this process 103 can then provide for adjusting the relative lateral X-ray beam position with respect to the detector to thereby improve the resolution of the corresponding scanned image. Such an adjustment can be effected as desired and/or in accordance with the capabilities of a given enabling platform. Pursuant to a preferred approach the adjustment occurs through steering of the X-ray beam (preferably on a sample-by-sample basis). Such steering can be achieved, if desired, using well understood prior art electromagnetic techniques in this regard.

Figure 10:
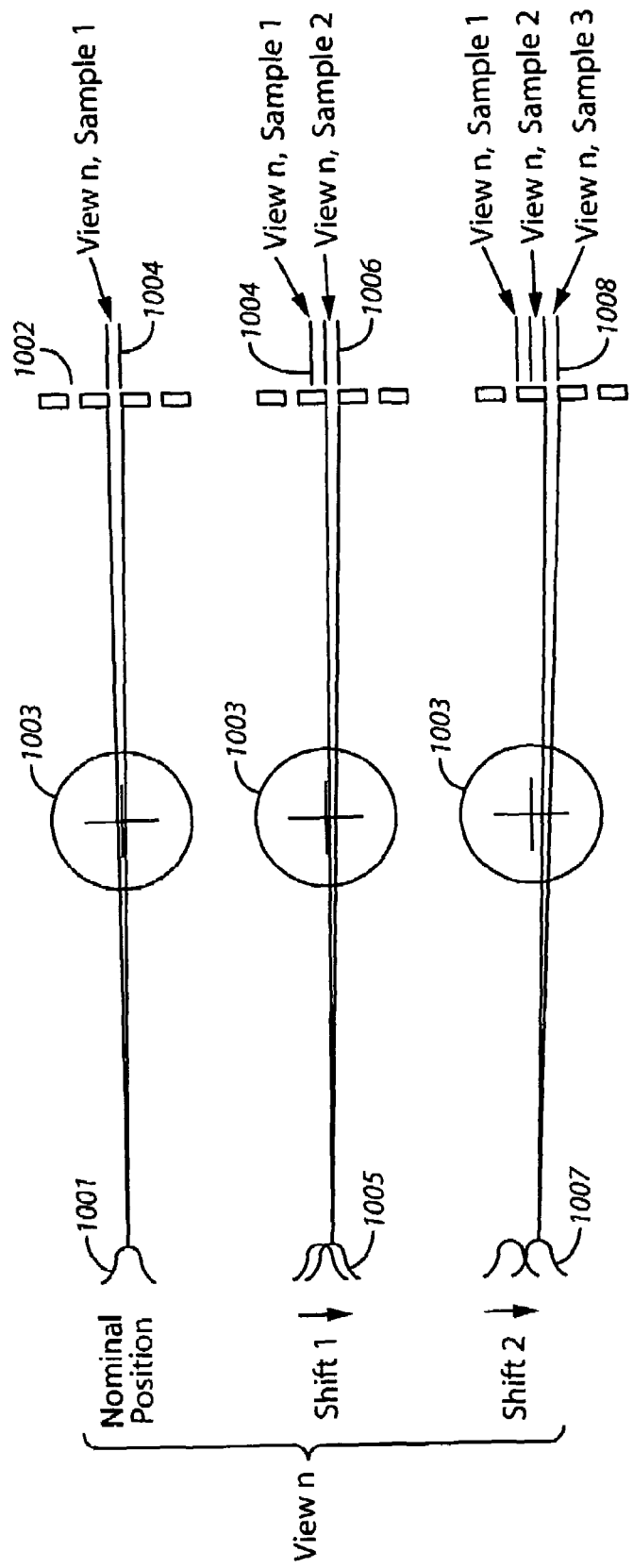
FIG. 10 comprises schematic depictions as configured in accordance with various embodiments of the invention.

To illustrate, and referring now to FIG. 10, the nominal position 1001 of an X-ray source will yield, at a corresponding detector 1002, a given view. For an nth view (where n is simply an integer), this given view comprises a first sample 1004 of view n as corresponds to a given focal spot 1003 of interest. Pursuant to these teachings, via steering or other adjustment mechanism of choice, the position of the X-ray source is slightly laterally shifted to a new shifted position 1005. Upon pulsing the X-ray source, the same detector 1002 will now capture a second sample 1006 for the same effective view n with respect to the focal spot 1003. This second sample 1006, however, is slightly askew with respect to the first sample 1004 and, in fact, contains image information not found in the first sample 1004. This increased information with respect to slightly adjacent image content contributes to a higher resolution view of the object being imaged.

This process can be continued if desired. For example, as shown, the X-ray source can again be slightly laterally shifted to a new shifted position 1007 that will, in turn, yield a third sample 1008 for view n to thereby further increase the amount of detail, granularity, and resolution information regarding this essential view of the object being imaged.

When used in combination with the helical scanning process described earlier and whilst the X-ray source is in continuous rotational motion, additional samples can be taken with appropriate lateral shifts of the X-ray source to improve the granularity of sampling. Hence a plurality of scans can be taken in the helical mode with improved resolution whilst maintaining the advantage of the helical scanning speed.

In general, total source spot movement will preferably be typically less than the detector pitch to permit filling of the gaps. Those skilled in the art will also understand that one could achieve these results by corresponding movement of the detectors. This would likely prove difficult during helical scanning, however, since this would typically require moving a very heavy object very quickly. In general, most practitioners will therefore prefer to effect this rapid movement of the focal spot by electromagnetic means.

Those skilled in the art will appreciate that the focal spot can also be moved in the axial direction thereby improving resolution in the slice direction.

Those skilled in the art will appreciate that the above-described processes can be used individually or in combination with one another to achieve great flexibility and capability with respect to capturing preliminary and/or full-scan computerized tomographic images of a wide variety of objects, including oddly-shaped objects, relatively large objects, and/or relatively opaque objects that require a large, powerful X-ray source. These benefits are attainable in an economical and relatively straightforward manner and can be deployed and utilized in a relatively rapidly effected process. Furthermore, all of these processes, alone or in combination with one another, can be employed with objects relatively independently of the object's orientation. This, in turn, permits the object to remain in a preferred orientation as versus requiring unique and sometimes inappropriate positioning of the object to suit the requirements of the imaging process.

Those skilled in the art will recognize that a wide variety of modifications, alterations, and combinations can be made with respect to the above described embodiments without departing from the spirit and scope of the invention, and that such modifications, alterations, and combinations are to be viewed as being within the ambit of the inventive concept.

We claim:

1. A method comprising:
    providing an X-ray source of radiation comprising a linear accelerator, wherein the X-ray source of radiation emits an X-ray beam having a corresponding illumination pattern;
    providing at least one radiation detector;
    providing an object to be scanned, which object has a cross-sectional girth that is larger than the illumination pattern;
    conducting a preliminary scan of the object by:
        substantially continuously causing the object to move in a first direction;
        while substantially continuously causing the object to move in the first direction, using the X-ray source of radiation and the at least one radiation detector to conduct a preliminary scan of the object, wherein using the X-ray source of radiation and the at least one radiation detector comprises:
            maintaining the X-ray source of radiation and the at least one radiation detector in a substantially fixed first position;
            using the at least one radiation detector to capture a plurality of scanned X-ray line images, wherein at least one of the plurality of scanned X-ray images comprises only a first incomplete part of a complete radiographic view of the object;
        moving the X-ray source of radiation and the at least one radiation detector to substantially fixed second positions, which second positions are different than the first positions by 180 degrees;
        substantially continuously causing the object to move in a second direction;
        while substantially continuously causing the object to move in the second direction, continuing to use the X-ray source of radiation and the at least one radiation detector to continue the preliminary scan of the object, wherein continuing to use the X-ray source of radiation and the at least one radiation detector comprises:
            maintaining the X-ray source of radiation and the at least one radiation detector in the substantially fixed second positions offset from the first by 180 degrees;
            using the at least one radiation detector to capture a second plurality of scanned X-ray images, wherein at least one of the second plurality of scanned X-ray images comprises only a second incomplete part of a complete radiographic view of the object;
        such that the first incomplete part and the second incomplete part, when joined to one another, comprise a complete radiographic view of the object;
    subsequent to conducting the preliminary scan of the object:
    substantially continuously causing the object to move;
    while substantially continuously causing the object to move, using the X-ray source of radiation and the at least one radiation detector to acquire a plurality of computerized tomography images of the object, wherein using the X-ray source of radiation and the at least one radiation detector comprises:
        substantially continuously concentrically moving the X-ray source of radiation and the at least one radiation detector about an axis of the object to effect helical movement of the X-ray source of radiation with respect to the object;
        determining whether to adjust a relative lateral position of the X-ray beam with respect to the at least one detector to thereby improve resolution of at least one of the plurality of computerized tomography images.

2. The method of claim 1 wherein providing an X-ray source of radiation comprises providing at least a 1 million volt X-ray source of radiation using a linear accelerator.

3. The method of claim 1 wherein determining whether to adjust a relative lateral position of the X-ray beam with respect to the at least one detector to thereby improve resolution of at least one of the plurality of scanned X-ray images further comprises, when determining to make an adjustment, steering the X-ray beam to thereby adjust the relative lateral position of the X-ray beam.

4. The method of claim 1 wherein determining whether to adjust a relative lateral position of the X-ray beam with respect to the at least one detector to thereby improve resolution of at least one of the plurality of scanned X-ray images further comprises, when determining to make an adjustment, adjusting the relative lateral position of the X-ray beam on a pulse-by-pulse basis.

5. The method of claim 1 wherein substantially continuously causing the object to move comprises substantially continuously causing the object to move along the axis of the object.

6. The method of claim 1 wherein the second direction is opposite to the first direction.

7. A method comprising:
providing an X-ray source of radiation comprising a linear accelerator, wherein the X-ray source of radiation emits an X-ray beam having an illumination pattern;
providing at least one radiation detector;
providing an object to be scanned, which object has a cross-sectional girth that is larger than the illumination pattern of the X-ray beam;
while substantially continuously causing the object to move in a first direction and while maintaining the X-ray source of radiation substantially stationary in a first position:
using the X-ray source of radiation and the at least one radiation detector to acquire a first plurality of line scan images of a first portion of the object, wherein the first portion of the object is less than a whole portion of the object;
while substantially continuously causing the object to move in a second direction and while maintaining the X-ray source of radiation substantially stationary in a second position that is substantially 180 degrees opposite to the first position:
using the X-ray source of radiation and the at least one radiation detector to acquire a second plurality of line scan images of a second portion of the object, wherein the second portion of the object is less than a whole portion of the object.

8. The method of claim 7 wherein the first direction is substantially identical to the second direction.

9. The method of claim 7 wherein the first direction is substantially opposite to the second direction.

10. The method of claim 7 wherein the first portion of the object in combination with the second portion of the object comprises a whole portion of the object.

11. The method of claim 10 wherein the first plurality of line scan images in combination with the second plurality of line scan images comprise a whole-cross-sectional digital radiography image of the object.

12. A method comprising:
providing an X-ray source of radiation comprising a linear accelerator, wherein the X-ray source of radiation emits an X-ray beam having a corresponding illumination pattern;
providing at least one radiation detector;
providing an object to be scanned, which object has a cross-sectional girth that is larger than the illumination pattern;
conducting a preliminary scan of the object by:
substantially continuously causing the object to move in a first direction;
while substantially continuously causing the object to move in the first direction, using the X-ray source of radiation and the at least one radiation detector to conduct a preliminary scan of the object, wherein using the X-ray source of radiation and the at least one radiation detector comprises:
maintaining the X-ray source of radiation and the at least one radiation detector in a substantially fixed first position;
using the at least one radiation detector to capture a plurality of scanned X-ray line images, wherein at least one of the plurality of scanned X-ray images comprises only a first incomplete part of a complete radiographic view of the object;
moving the X-ray source of radiation and the at least one radiation detector to substantially fixed second positions, which second positions are different than the first positions by 180 degrees;
substantially continuously causing the object to move in a second direction;
while substantially continuously causing the object to move in the second direction, continuing to use the X-ray source of radiation and the at least one radiation detector to continue the preliminary scan of the object, wherein continuing to use the X-ray source of radiation and the at least one radiation detector comprises:
maintaining the X-ray source of radiation and the at least one radiation detector in the substantially fixed second positions offset from the first by 180 degrees;
using the at least one radiation detector to capture a second plurality of scanned X-ray images, wherein at least one of the second plurality of scanned X-ray images comprises only a second incomplete part of a complete radiographic view of the object;
such that the first incomplete part and the second incomplete part, when joined to one another, comprise a complete radiographic view of the object;
subsequent to the preliminary scan of the object:
substantially continuously causing the object to move;
while substantially continuously causing the object to move, using the X-ray source of radiation and the at least one radiation detector to acquire a plurality of computerized tomography images of the object by substantially continuously concentrically moving at least the X-ray source of radiation about an axis of the object to effect helical movement of the X-ray source of radiation with respect to the object.

13. The method of claim 12 wherein substantially continuously causing the object to move comprises substantially continuously causing the object to move along the axis of the object.

14. The method of claim 12 wherein substantially continuously concentrically moving at least the X-ray source of radiation about an axis of the object further comprises substantially continuously concentrically moving the at least one radiation detector about the axis of the object.

* * * * *